United States Patent [19]

French et al.

[11] 4,121,099
[45] Oct. 17, 1978

[54] METHOD AND APPARATUS FOR FOCUSSING AND DECLUSTERING TRACE IONS

[75] Inventors: John Barry French; Neil M. Reid, both of Thornhill; Janette A. Buckley, Willowdale, all of Canada

[73] Assignee: The Governing Council of the University of Toronto, Toronto, Canada

[21] Appl. No.: 790,216

[22] Filed: Apr. 25, 1977

Related U.S. Application Data

[63] Continuation-in-part of Ser. No. 555,202, Mar. 3, 1975, Pat. No. 4,023,398.

[51] Int. Cl.² ............................................. B01D 59/44
[52] U.S. Cl. ..................................... 250/296; 250/281
[58] Field of Search ................ 313/309, 336; 250/281, 250/296

[56] References Cited

U.S. PATENT DOCUMENTS

| 2,287,749 | 6/1942 | Slayter | 313/309 |
|---|---|---|---|
| 2,631,255 | 3/1953 | Stavro | 313/336 |
| 3,920,987 | 11/1975 | Anbar et al. | 250/281 |
| 4,031,397 | 6/1977 | Cardillo | 250/281 |

*Primary Examiner*—Harold A. Dixon
*Attorney, Agent, or Firm*—Rogers, Bereskin & Parr

[57] ABSTRACT

A method and apparatus for focussing and declustering trace ions travelling from a gas through an orifice into a vacuum chamber and to a mass analyzer in the vacuum chamber. Advantage is taken of the free jet expansion of the gas into the vacuum chamber by applying an electric focussing field in a specific region of the free jet. The region is selected sufficiently close to the orifice that the gas density limits the kinetic energy spread which the ions can acquire under the applied field, typically to 2 ev or less, while the early focussing increases the available ion signal. Declustering can be collision induced in the region by providing a field in the region sufficient to impart an internal energy of between 0.1 and 1.5 ev to ions in the region. The kinetic energy which the ions can acquire under the applied field is still limited by the density of the gas in the free jet, so that the kinetic energy spread which the ions can acquire is still limited. Preferably the focussing and declustering fields are produced by a single conical tapered lens element located at distance $X_l$ from the orifice, where $$X_l = 50D^{+40D}_{-25D}$$

and D is the orifice diameter, for atmospheric pressure and room temperature source conditions. The electric field between the lens element and the mass spectrometer is then controlled to limit the energy spread imparted to the ions in their travel from the lens elements to the mass spectrometer.

17 Claims, 10 Drawing Figures

METHOD AND APPARATUS FOR FOCUSSING AND DECLUSTERING TRACE IONS

This application is a continuation-in-part of our U.S. patent application Ser. No. 555,202 filed Mar. 3, 1975 now U.S. Pat. No. 4,023,398 issued May 17, 1977 and entitled "APPARATUS FOR ANALYZING TRACE COMPONENTS".

This invention relates to a method and apparatus for analyzing trace ions using an analyzer located in a vacuum chamber. More particularly the invention relates to a method and apparatus for achieving improved focussing of such ions. In one aspect the invention also relates to a method and apparatus for reducing clustering of neutral molecules about the trace ions. The method and apparatus of the invention can in one aspect also be used for achieving fragmentation of the ions.

In the analysis of trace components, high or atmospheric pressure ion sources have become known. For example, atmospheric pressure chemical ionization sources are used in mass spectroscopy. It has been well documented that in the use of such sources, clustering of neutral molecules about the ions can occur in the reaction region where the ions are created. In addition, the ions must enter the vacuum chamber through an orifice, and high pressure gas expands through this orifice into the vacuum chamber. As the gas expands, it cools rapidly, and clustering of gas molecules about the ions commonly occurs during the expansion.

The clustering of atoms and molecules about the ions to be analyzed is generally undesirable because for each ion species to be measured, the clustering adds additional spectral peaks in the observed mass spectrum. This complicates the interpretation when mixtures are being analyzed and will reduce or can even eliminate the available signal corresponding to the desired unclustered ion. The clustering propensity is particularly high for readily condensible gases such as water vapour, but there can also be significant clustering in the presence of such gases as nitrogen and argon.

A further problem that occurred in the past is that when the ions entering the vacuum chamber were focussed into the mass analyzer, a large kinetic energy spread was sometimes imparted to the ions by the focussing process. The energy spread caused serious degradation of the mass analyzer resolution. To reduce the energy spread, energy filters or lower focussing voltages may be used, but both these techniques result in a much reduced ion signal.

Accordingly, it is an object of the present invention in one of its aspects to provide improved ion focussing with a reduced energy spread. This is achieved by applying a focussing electric field to the ions in a specific region of the free jet expansion of the sampling gas into the vacuum chamber. Specifically, an electric field is provided to focus the ions in a selected region of the free jet sufficiently close to the orifice that the ions cannot acquire a kinetic energy spread greater than a predetermined maximum value therein under the applied field. This value will depend on the resolution desired to be obtained from the mass analyzer. In a good quality quadrapole mass spectrometer, an energy spread greater than about 2 ev tends to degrade the ability to resolve adjacent mass peaks one a.m.u. apart. In the selected region of the free jet the gas is sufficiently dense that collisions between ions and gas molecules are frequent, thus limiting the kinetic energy which the ions can acquire in the region and thereby limiting the kinetic energy spread which the ions can acquire. The electric fields applied downstream of this selected region are controlled to limit the energy spread imparted thereafter to the ions.

In a second aspect of the invention, an electric field is applied to the ions in the previously mentioned region, of sufficient strength to impart to the ions internal energy adequate to break cluster bonds without breaking chemical bonds. Typically the field will be sufficient to impart on internal energy in the range between 0.1 and 1.5 ev. Any electric fields then applied downstream of the selected region are still controlled to limit the energy spread imparted thereafter to the ions.

If a large energy spread is acceptable, then the field in the selected region can be increased sufficiently to break chemical as well as cluster bonds, thereby fragmenting the original ions. This produces spectra similar to electron impact spectra.

The combined early focussing and declustering, which can be achieved by several properly placed electrostatic lens elements, or, in a preferred embodiment, by a single such lens element, greatly increases the unclustered ion signal into the mass analyzer.

Preferably the gas admitted into the vacuum chamber during the free jet expansion is cryopumpable and is pumped by cooling a surface in the vacuum chamber. This permits a larger free jet. The larger free jet facilitates construction and positioning of the electric field generating means used to focus and decluster the ions and also permits a larger ion signal into the vacuum chamber.

Further objects and advantages of the invention will appear from the following description, taken together with the accompanying drawings, in which.

Figure 1A:
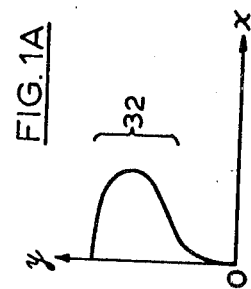
FIG. 1A illustrates the ion profile with respect to a radioactive foil
Figure 1:
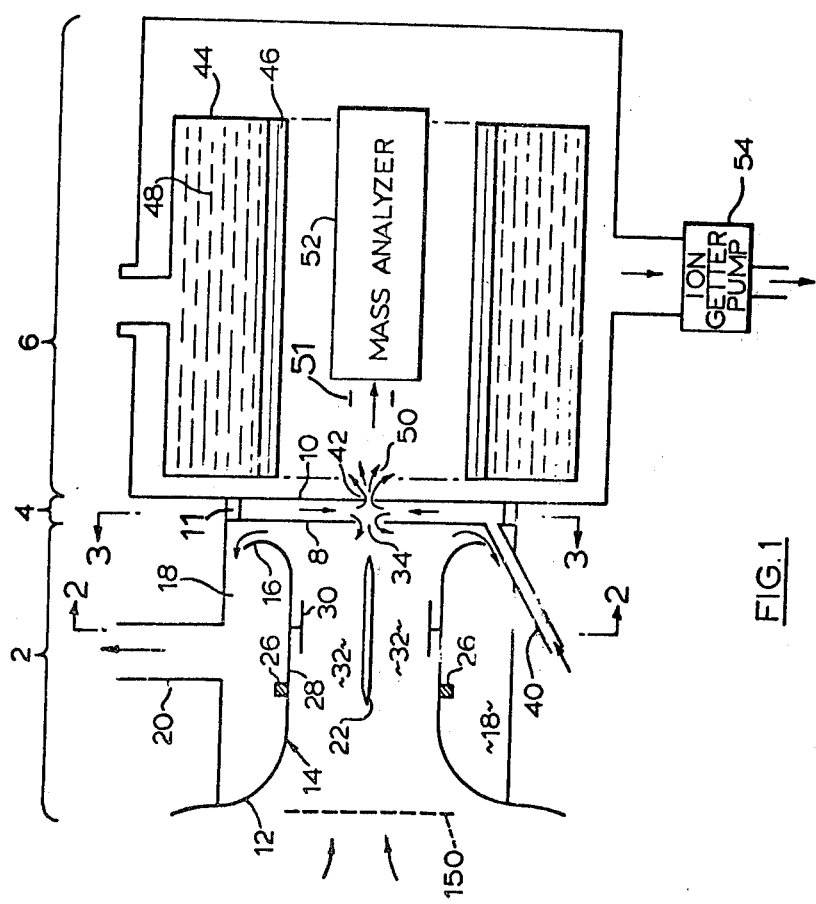
FIG. 1 is a diagrammatic sectional view showing a mass spectroscopy system in which the present invention may be used.

Reference is first made to FIGS. 1 to 4, which show a typical mass spectroscopy system with which the present invention may be used. The system shown in FIGS. 1 to 4 is that shown in our U.S. Pat. No. 4,023,398.

The apparatus of FIGS. 1 to 4 includes an ion reaction section generally indicated at 2, a gas curtain section 4, and a vacuum chamber (and analyzing) section 6. The reaction section 2 and the gas curtain section 4 are connected by an interface plate 8, while the gas curtain section 4 and the vacuum section 6 are in turn connected by an orifice plate 10.

The reaction section 2 includes a bellmouth inlet 12 and a cylindrical duct 14 connected at 16 to a plenum 18. The plenum 18 is connected by duct 20 to a synchronous fan (not shown) which operates to draw the air or other gas to be analyzed through the bellmouth inlet 12 and into the duct 14. Settling screens (not shown) may be provided in advance of the the inlet 12 to eliminate vortices and to help provide laminar flow.

Figure 2:
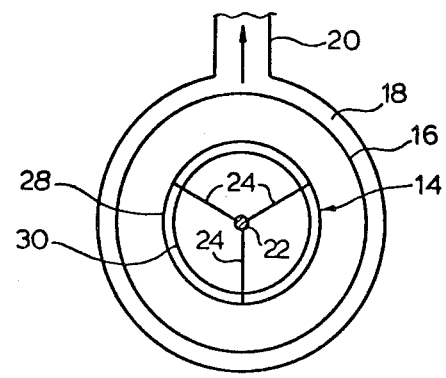
FIG. 2 is a sectional view along lines 2—2 of FIG. 1.

Located in the duct 14 is a central axially elongated electrode 22. The electrode 22 is supported in a position aligned with the axis of duct 14 by a triangular spider of insulating material such as nylon thread 24, as shown in FIG. 2. A separate insulated wire, not shown, is used to apply a desired voltage to the electrode 22. The portion of the duct 14 which surrounds the electrode 22 is insulated from the bellmouth 12 by an insulating joint diagrammatically indicated at 26, so that the wall portion of the duct 14 downstream of the joint 26 forms a second or outer electrode 28. Located between the two electrodes 22, 28 is ring-shaped ionizing device 30 such as a tritium foil.

In operation, air or other carrier gas containing the trace gas to be analyzed is drawn into the cylindrical duct 14 by the synchronous fan at a rate such as to provide a flow which is laminar but which is of sufficiently high velocity to minimize the effects of species diffusion. As the mixture passes the ionizing device foil 30, ion creation occurs in the region 32, forming a mixture of positive and negative ions in the gas. The ion creation region 32 is annular in form and its profile is shown in FIG. 1A, where distance from the foil is plotted along the Y axis (the foil being located at the origin) and the relative number of ions formed is plotted along the X axis.

During the ion creation, the beta rays from the tritium foil ionize components of the air or other carrier gas, resulting (after a series of reactions in the air or carrier gas) in the production of primary reactant ions. Some of the primary reactant ions then react with molecules of the trace gas to form trace ions from the trace gas. This results in a mixture of trace ions and reactant ions. From this mixture, the trace ions are to be preferentially selected and analyzed.

An electric field, caused by appropriate potentials applied to the electrodes 22 and 28, the interface plate 8, and the orifice plate 10, is superimposed on the fluid flow. Ions are thus caused to drift with a local velocity $\vec{V_1} = \vec{V_f} + K\vec{E}$, where $\vec{V_f}$ is the local fluid velocity, $\vec{E}$ is the local electric field vector and $K$ is the mobility of the species in question. The potentials applied to the device, and the geometry of the device, are arranged such that the desired ions of selected polarity and any mobility are caused to converge in an approximately conical fashion from the reaction region 32 to a central region downstream of the front of the central electrode 22 and generally aligned with the axis of the electrode 22. The desired ions are thence carried forward in a concentrated flux toward a central aperture 34 in the interface plate 8. A portion of the ions originating from the sample flowing through the reaction region 32 passes through the central aperture 34 in the interface plate.

Figure 3:
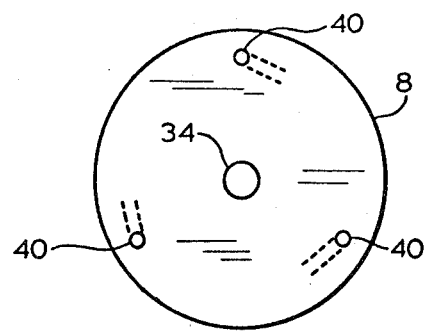
FIG. 3 is a sectional view along lines 3—3 of FIG. 1.
Figure 4:
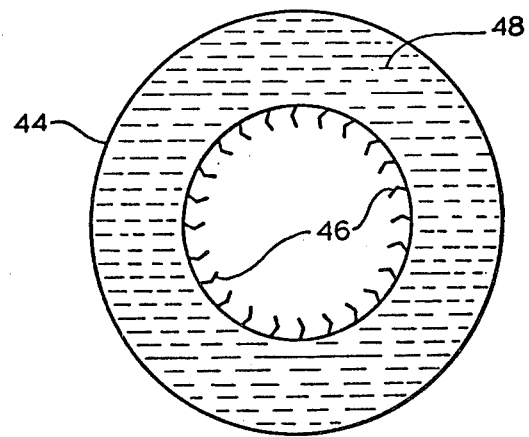
FIG. 4 is a sectional view of the cryopump of FIG. 1.

The transfer of the concentrated ions into the vacuum and analyzer section 6 is accomplished by means of the gas curtain section 4 and by cryogenic pumping in the vacuum section 6. Specifically, the gas curtain section 4 is supplied with an appropriate gas (such as $CO_2$ or argon) which is selected to minimize reactions with the ions to be sampled and which can be conveniently cryopumped in the vacuum section 6. The curtain gas is selected to have a vapour pressure substantially less than atmospheric (typically $10^{-4}$ torr or less) at a temperature to which the vacuum chamber walls can conveniently be cooled. The curtain gas acts as a curtain or gas membrane between the reaction section 2 and the vacuum section 6, and is directed into the gas curtain section 4 by inlet ducts 40 arranged to create a generally circular flow pattern having a circumferential component but directed generally radially inwardly in the gas curtain section 4 (FIG. 3). The curtain gas is supplied at sufficient flow to match the ingestion into the vacuum section 6 and to provide a small excess which effuses gently out through the central hole 34 in the interface plate 8, at sufficient flow to prevent passage of the carrier gas into the space between the interface plate 8 and the orifice plate 10. However, the concentrated ion flux is drawn forward, counter to this gentle outflow of curtain gas, by an appropriate attractive potential on the orifice plate 10, until these ions are caught up by the portion of the curtain gas flowing through the orifice 42 of the orifice plate and hence are carried into the vacuum section.

The vacuum section 6 includes (see also FIG. 4) a cooling fluid reservoir 44 having fins 46. The reservoir 44 conveniently contains liquid nitrogen 48. As the curtain gas, containing the ions of interest, expands outwardly from the orifice 42, the curtain gas molecules impinge on the fins 46 and deposit there, reducing the pressure in the vacuum chamber. The fins 46 are formed with appropriate trapping surface geometry, as is well known in the art of cryopumping, to maximize the trapping and depositing of the curtain gas molecules. By this means, a high pumping speed can be achieved, so that an operating vacuum in the $10^{-5}$ to $10^{-6}$ torr range (suitable for mass spectrometry) can be obtained with an entry orifice 42 diameter of about 0.033 cm. This size is substantially larger than the 0.002 cm maximum or smaller size orifices conventionally used, so that the ion flux into the vacuum section can be increased at least by the ratio of hole areas, typically by several hundred or more.

Once a vacuum has been established (a mild vacuum may initially be created by convenient conventional means, e.g. a small mechanical roughing pump, and then increased by cryopumping), the curtain gas entering the vacuum section 6 expands in a free jet 50. The ions entering the vacuum section also expand in the free jet 50 but are focussed by electrostatic ion lens elements (to be discussed) into a mass analyzer 52 such as a quadrapole mass spectrometer. The mass analyzer 52 analyzes the ions according to their charge-to-mass ratio and allows quantitative determination by ion counting or other appropriate conventional techniques. A small additional vacuum pump 54 may be provided to remove non-condensable impurities (such as nitrogen) from the vacuum chamber. The pump 54 conveniently may be a getter ion pump.

A conventional method of focussing used in the past was to place electrostatic lens elements well downstream of the orifice 42 and to place relatively high voltages on those lens elements relative to the orifice plate, to focus the ions into the mass analyzer. When an adequate vacuum ($10^{-3}$ torr or less) is maintained in the vacuum chamber, the applicants have determined that such focussing will cause a substantial energy spread in the ions introduced into the mass analyzer, causing degradation of the resolution of the analyzer and affecting detectability.

The applicants have discovered that by controlled application of an electric field in a specific region of the free jet 50, good early focussing of the ions can be achieved while at the same time imparting an acceptably small energy spread to the ions to be analyzed. The applicants have also found that an electric field can be applied in a downstream portion of the specific region of the free jet 50 to achieve a desirable variable amount of declustering, while still limiting the energy spread imparted to the ions.

Figure 5:
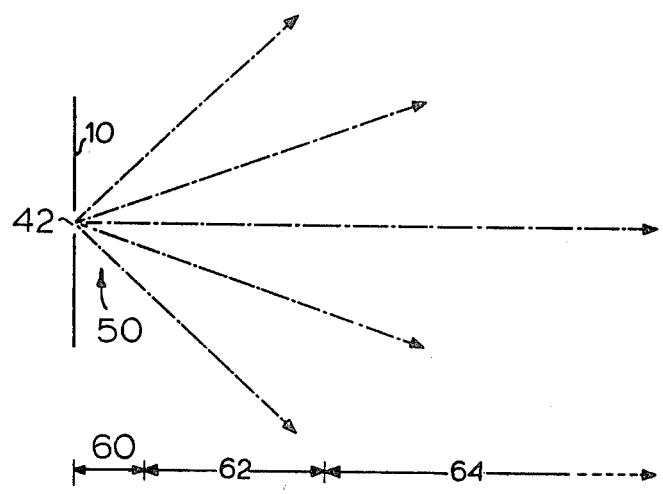
FIG. 5 is a sectional view showing certain regions in the vacuum chamber of the FIG. 1 system.

More specifically, and with reference to FIG. 5, the expanding curtain gas jet, indicated at 50 in FIG. 5, may be characterized as having three zones, indicated at 60, 62, 64 in FIG. 5. In zone 60, which may be called the continuum zone, the gas jet, although rapidly expanding, is still relatively dense. In this zone, electric fields can be applied to alter the trajectory of the ions without imparting substantial kinetic energy to the ions.

In zone 62, which may be called the transition zone, the density of the gas jet is much reduced, and the ions are able to accumulate larger amounts of energy if an electric field is applied to yield appropriate $E/n$ values where E is the electric field in volts per cm. and $n$ is the gas number density. At the same time, there are enough gas molecules present so that some collisions with the neutral gas molecules in the free jet are still occurring. In general, zone 162 may be defined as a zone in which declustering and ion fragmentation may occur.

The third zone 164 may be referred to as the vacuum trajectory or free molecular flow zone. Here, the gas molecules have become so rarified that the likelihood of collisions between ions and these gas molecules is very low. This is the zone in which conventional focussing screens and electrostatic lens elements, including any appropriate vacuum ion lens configuration, may be used. The mean free path of ions in zone 164 may be of the order of a few centimeters or greater (typically 2 cm or more).

Figure 6:
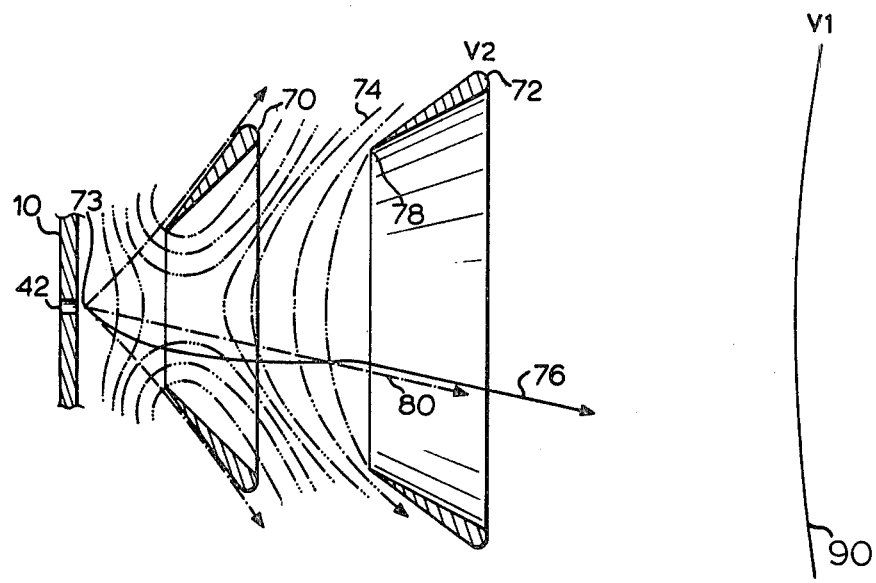
FIG. 6 is a sectional view showing an arrangement of focussing elements in the regions shown in FIG. 5.

As shown in FIG. 6, advantage of the existence of the zones can be taken by providing appropriate focussing elements in zone 60. In zone 60, the curtain gas (and with it the ions) is expanding in a wide cone, most of the ions however being contained within a 90 degree whole angle cone because the flux of ions is distributed according to a cosine squared law. Accordingly, an electrostatic lens is provided, formed by two conical tapered rings 70, 72. The rings 70, 72 are supported by fine wires (not shown) and are aimed approximately at the orifice 42 to minimize interference with the expanding gas. Since the actual expansion of the curtain gas occurs in a cone whose vertex is displaced slightly outwardly from the orifice plate 10, the cones subtended by the rings 70, 72 may in fact have their vertices at an origin or point 73 spaced slightly outwardly of the orifice plate 10 (by less than one orifice diameter).

When appropriate potentials are applied to the rings 70, 72 relative to the orifice plate 10, a saddle shaped field can be created, indicated by field lines 74 (which of course show the field only in two dimensions). The trajectory of a typical ion is indicated at 76. Ions whose initial trajectories are outside the rings 70, 72 are lost, but these ions are very few in number. Ions whose initial trajectories are at less than 45 degrees to the axis of the system are deflected inwardly until after they have passed the leading edge 78 of cone 72. At this point, the field created by the voltages applied to the rings ceases to affect the ions. The ions now enter zones 62 and assume the direction of movement of the expanding gas jet 80. The result of this is that the ions initially in a 90° whole angle cone are concentrated into a much smaller whole angle cone, e.g. about 30° to 45°, so that more of the ions can be focussed in zone 64 so as to travel into the mass spectrometer. Because the energy which the ions can acquire in zone 60 is so limited, the kinetic energy spread imparted to the ions by the focussing in zone 60 is minimal.

Figure 7:
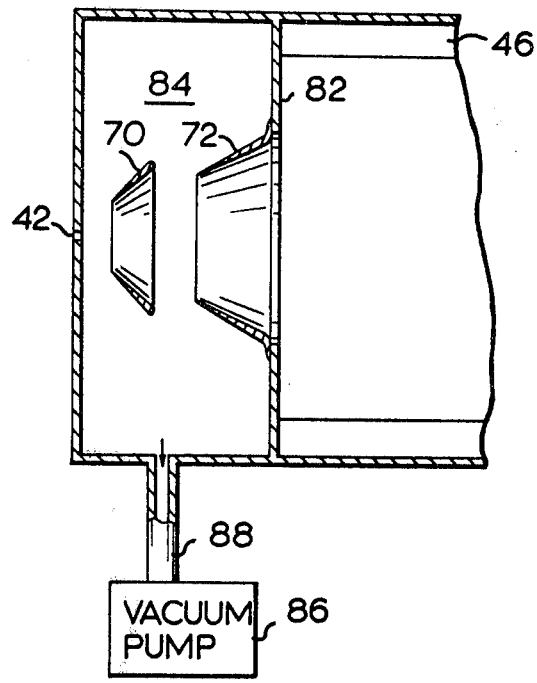
FIG. 7 is a sectional view showing a modification of the FIG. 6 arrangement.

An added advantage of the approach described above results from the fact that a substantial separation of the ions from the gas flow has been achieved at relatively high pressures. Therefore, pressure staging can be utilized to pump away the large fraction of the gas flow external to the cone into which the bulk of the ions have been focussed. An example of such pressure staging is shown in FIG. 7, where the second ring 72 is extended and mounted on a separator plate 82 to form a plenum 84 in zone 60 and from which gas can be pumped at relatively high pressure. Gas is exhausted from the plenum 84 to the pump 86 via duct 88. This reduces the load on the vacuum pump means (usually a cryopump) used for the remainder of the vacuum chamber. This permits a larger orifice for a given size of cryopump, or a small cryopump for a given orifice size.

By judicious choice of the voltages applied in zone 60, clustering reactions can to some extent be controlled. In zone 60, even though the ions cannot acquire substantial energy, they do acquire some energy. The energy can be controlled to reduce the likelihood of ions and molecules sticking together (clustering) when they collide, and to break apart some clusters that are bound loosely together by very low energy bonds. The geometry of zone 60 (i.e. the spacing, dimensions and angles) of rings 70, 72 or of any other appropriate lens elements used, may also be varied depending on the application of the system.

Screens such as screen 90 (shown in FIG. 6) may be placed in zone 62 to accelerate ions to produce interactions. By proper choice of the voltage V1 on screen 90 relative to the voltage V2 on ring 72, clustering can be controlled in zone 62. If V1 = V2, there is no potential difference between ring 72 and screen 82 and no declustering will normally occur between ring 72 and screen 82. Alternatively, voltage V2 can be made sufficiently different from voltage V1 so that enough energy is provided to break relatively loose clusters, or if desired, to break apart clusters or ions with higher energy bonds.

In summary at this point, it will be appreciated that in the embodiment of the invention just described, the early focussing in a relatively dense region of the free jet 50 will substantially increase the available ion signal into the mass spectrometer, as compared with focussing farther from the orifice, and at the same time, because the energy which the ions can acquire in this region is limited, the kinetic energy spread imparted to the ions is also limited. It will also be appreciated that by placing the screen 90 in a suitable location in zone 62 of the free jet and applying an appropriate field, at least some declustering can be achieved while still limiting the energy spread of the ions. Of course, the farther out screen 90 is placed in zone 62, the less dense will be the gas, so that ions will travel farther between collisions and will acquire a greater kinetic energy spread. How far out in zone 62 screen 82 can be placed will depend on the spectrum being analyzed; for simple spectra with only a few widely separated peaks, a larger kinetic energy spread can be tolerated than for more complex spectra with multiple close peaks.

Figure 8:
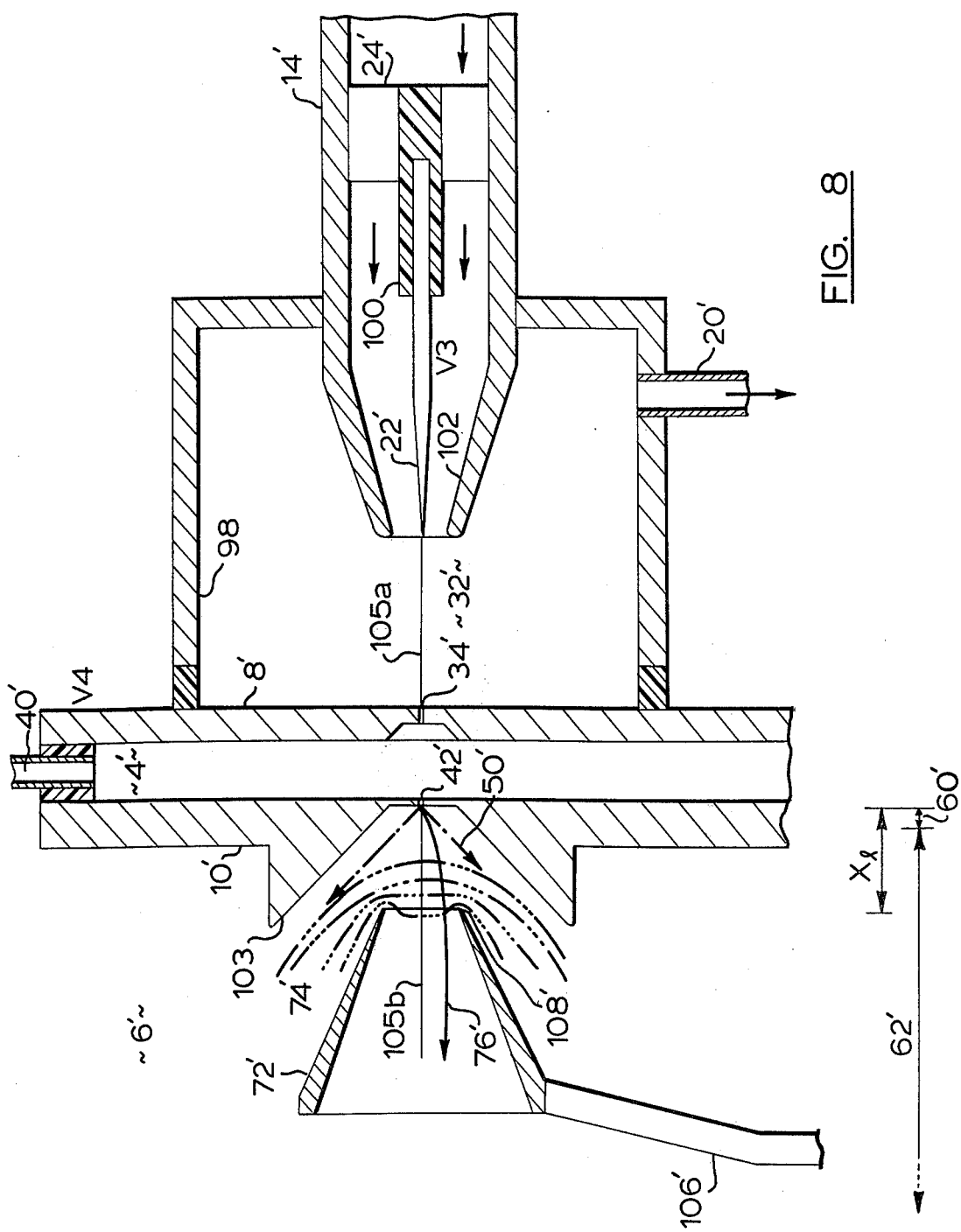
FIG. 8 is a sectional view showing another embodiment of the invention.
Figure 9:
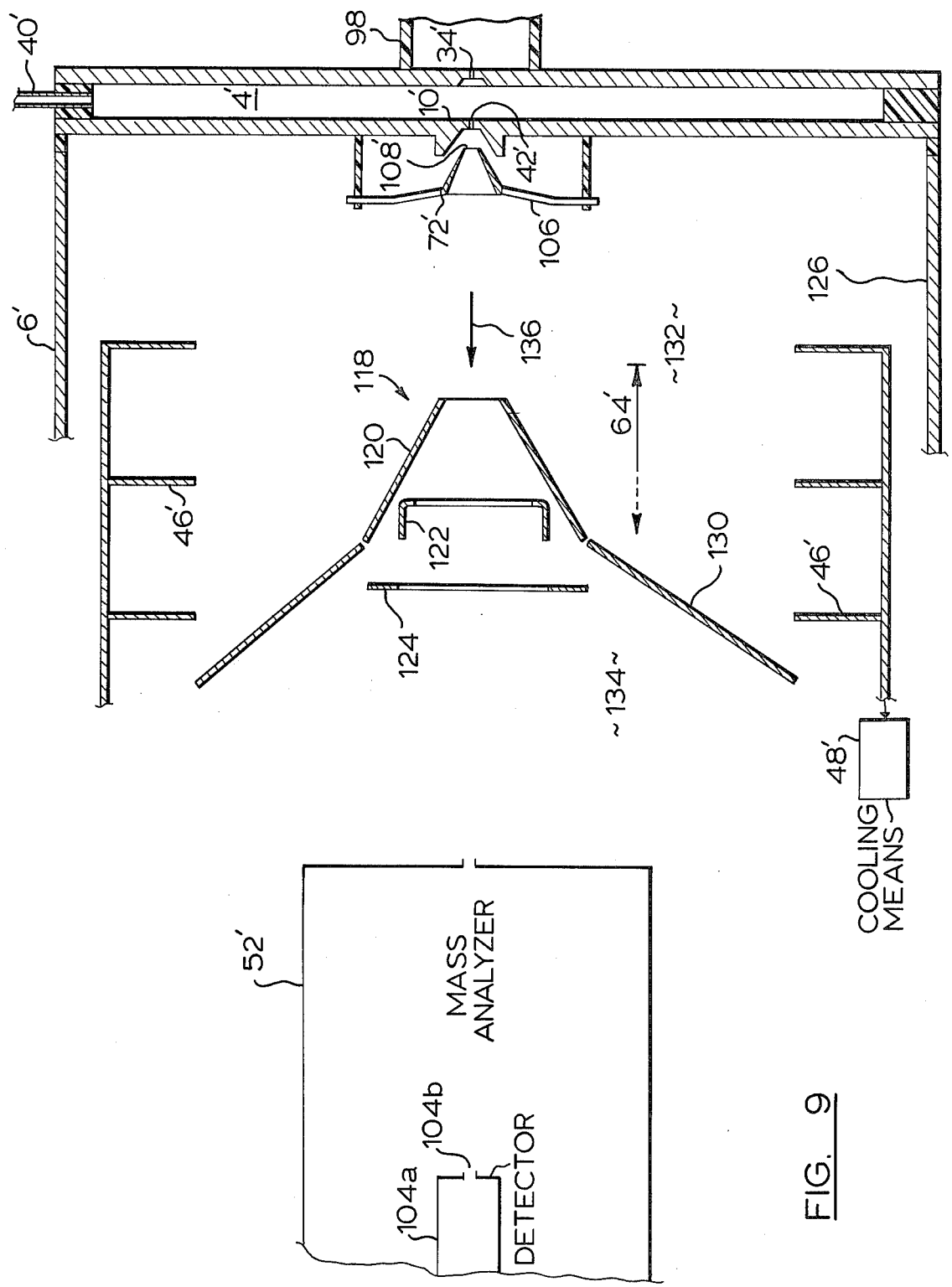
FIG. 9 is a sectional view showing further aspects of the FIG. 8 embodiment.

Reference is next made to FIGS. 8 and 9, which show another embodiment of the invention. In FIGS. 8 and 9, primed reference numerals indicate parts corresponding to those of FIGS. 1 to 7.

As shown in FIG. 8, sample gas, which consists of a carrier gas containing the trace molecules to be analyzed, is introduced, via a narrow cylindrical tube or shroud 14' into a reaction region 32' in a cylindrical chamber defined by plate 8' and wall 98. An electric discharge needle 22' is axially mounted in the tube 14' by an insulating support 100 and narrow support arms 24'. An appropriate potential V3 is applied to needle 22' relative to the potential V4 applied to the interface plate 8' to create a corona or other electric discharge from the tip of the needle 22'. Typically the sample gas will contain a chemical reagent gas, such as water vapour, isobutane, benzene, methylene chloride, or other appropriate reagent, which is ionized by the electric discharge between the tip of the needle and the interface plate 8. The reagent ions react with the trace molecules at the atmospheric pressure prevailing in the reaction region 32', to produce trace ions. The applicants have found that the ionizing discharge at the tip of the needle 22' is stablized by the stream of sample gas passing over the needle. The stabilization is improved by the narrowed or inwardly converging tip 102 of the tube or shroud 14', which causes the sample gas streamlines to converge as they pass over the tip of the needle 22'.

The ions produced in the reaction region 32' are drawn by a suitable attractive potential placed on the interface plate 8' through the opening 34' in the interface plate and into the gas curtain chamber 4'. The gas curtain chamber 4' is separated from the vacuum chamber 6' by an orifice plate 10' containing the orifice 42'. The downstream side of the orifice plate 10' preferably has an outwardly diverging conical surface 103 which helps to constrain gas expanding in the free jet 50' so that the gas travels in a direction most appropriate for pumping.

As before, an appropriate curtain gas, for example argon or nitrogen, is supplied via inlet 40' into the gas curtain chamber 4' at a pressure sufficient to block flow of the sample gas into the gas curtain chamber. The flow of gas into the gas curtain chamber 4' is sufficient so that a small excess effuses out opening 34' into the reaction chamber 32', where it and the excess sample gas are exhausted via duct 20'. The remainder of the curtain gas, together with the trace ions admitted into the gas curtain chamber, flow through the orifice 42' into the vacuum chamber. If the sample gas is cryopumpable, then the curtain gas may be eliminated or its flow may be controlled to control, but not entirely block, the flow of sample gas into the vacuum chamber. An appropriate potential is applied to the orifice plate 10' to assist in drifting the ions through the orifice 42'.

It is found that when the axis of the needle is aligned with the opening 34' and orifice 42', photons resulting from ultraviolet radiation from the needle 22' will enter the vacuum chamber 6' and cause "noise" by ejection of photo electrons from the ion detector 104a (FIG. 9) used in the mass analyzer 52' (FIG. 9). The applicants has found that this noise can be drastically reduced by offsetting the axis 105a of the needle 22' slightly from the axis 105b passing through opening 34', orifice 42' and the aperture 104b (FIG. 9) to the detector 104a. The offset will typically be only a few orifice diameters (the orifice diameter is typically 0.002 to 0.004 inches) and it is found that the slight offset has a negligible effect on the transmission of ions into the vacuum chamber. Since aperture 34' may typically be about ⅛ inch diameter, the offset optical line of sight between orifice 42' and aperture 104b (which may be 0.25 inch dimeter but is typically 10 inches downstream from orifice 42') provides the main constraint on transmission of photons into detector 104a.

As before the cooling surfaces or fins 46' of the vacuum chamber 6 are cooled by an appropriate cooling fluid, or by mechanical refrigeration, to a temperature sufficiently low to condense the gas entering the chamber 6.

Located in zone 62' of the vacuum chamber is a truncated tapered conical lens element 72'. As before, the cone of the lens element 72' is aimed at the orifice 42' or at a point just slightly downstream of the orifice 42'. The lens element 72' is supported by three spaced arms 106 of small diameter so as to interfere as little as possible with the gas flow.

In FIG. 8 the electric field lines produced between the upstream edge or entrance 108 of lens element 72' and the orifice plate 10' are indicated at 74', and the ion paths are shown at 76'. (Without focussing, the ion paths would diverge radially outwardly in the same manner as the free jet.) Since ions tend to follow paths orthogonal to the electric field lines, focussing occurs in zone 60' and to some extent in zone 62'. Although no specific lens element has been placed in zone 60', lens element 72' which is located in zone 62' performs the functions of both lens elements 70, 72 shown in FIG. 6. The situation is the same as that which would prevail if, instead of placing a slightly repulsive voltage on lens element 70, an attractive potential (a voltage part way between that of plate 10 and element 72) were placed on element 70. At such an intermediate voltage, the functions of lens elements 70, 72 can be performed by the single lens element 72' of FIG. 8. In addition, lens element 72' also performs the functions of lens element 90 of FIG. 6.

As indicated previously, the positioning of lens element 72' in the transition zone 62' of the free jet 50' will depend on the performance desired. If the entrance to lens element 72' is too far downstream, then when sufficient potentials are applied to eliminate significant clustering, the ion kinetic energy spreads produced will be too high for use in analysis of complicated spectra. However, a position relatively far downstream in zone 62' may still be suitable for analysis of simple spectra. As previously indicated, if the entrance 108 to lens element 72' is placed too far upstream in zone 62, then it may be difficult to apply enough energy to the ions to cause the desired degree of declustering.

The applicants have determined that an ion kinetic energy spread less than 2 ev is normally needed to resolve clearly mass peaks 1 a.m.u. (atomic mass unit) apart with existing quadrupole mass spectrometers. The entrance 108 of lens element 72' will therefore be set sufficiently close to the orifice 42' that this energy spread is not exceeded under the field applied between the lens element and the orifice plate. The entrance 108 can be set in continuum zone 60 to achieve this requirement while achieving early focussing.

However, for declustering, an internal energy of between 0.1 and 1.5 ev must be imparted to the ions. (Of course, internal energies greater than 1.5 ev will also produce declustering but will be associated with kinetic energy spreads larger than are normally necessary.) To impart this much energy to the ions, the entrance 108 will normally be set not in zone 60' but instead in the transition zone 62', at a location where the gas density is low enough to permit acquisition by the ions of the desired internal energy, through collisional actuation, but is still high enough to limit the kinetic energy spread acquired by the ions (preferably to 2 ev or less).

The applicants have determined that to meet the above criteria, the following parameters will normally be applicable. Firstly the field created between the orifice plate 10' and the lens 72' will not be so great as to cause a discharge between them. Since lens 72' is a sharp cone and is close to orifice plate 10', with substantial pre-ionized gas between them, this limits the maximum voltages to be applied. At the same time the fields should be sufficient for the purposes previously mentioned. Secondly, for a source gas (i.e. the gas in the gas curtain chamber where a gas curtain is used) having a number density of $2.7 \times 10^{19}$ molecules per cubic centimeter, the distance $X_l$ along the axis 50b between the orifice 42' and the entrance 108 of the lens element 72' is best given by the relationship $$X_l = 50D^{+40D}_{-25D}$$

where D is the diameter of the orifice 42'. At this location of the entrance 108, the gas density is high enough so that the ions will collide with molecules frequently enough so as not to acquire an undue energy spread, but the gas density is also low enough that the ions will be able to acquire enough energy to cause substantial declustering.

If the number density of the source gas increases (for example if the curtain gas pressure is more than one atmosphere of if the curtain gas is at a low temperature), then the optimum positioning of entrance 108 of the lens element 72' will be further downstream in zone 62. If the number density of the curtain gas is decreased, then the optimum positioning of the entrance 108 to lens element 72' is closer to the orifice. The gas number density $n$ in the free jet at any distance X from the orifice 42' is given by $$n = \frac{n_s \cdot .161 \cos^2(1.51\Theta)}{(X/D)^2}$$

where
$n_s$ is the source gas number density,
$\theta$ is the angle from the axis 105b, and
D is the orifice diameter.

From this relationship it will be seen that if the number density of the source gas varies by the factor $m$, then distance $X_l$ will vary by $\sqrt{m}$. In other words, $$X_l = [50D \pm \frac{40D}{25D}] \sqrt{m}$$

in this case.

The tolerance of $$+ 40D \\ - 25D$$

will depend upon the energy spread acceptable in the particular application of the invention. If a complex spectrum is to be analyzed, very little ion energy spread will be desired and the entrance 108 of the lens element 72' will be located no more than 50D from the orifice, and possibly as little as 25D from the orifice. If only a few ions are being analyzed, with widely separated peaks, then a larger energy spread can be tolerated.

It will be appreciated that in the application of the invention, the focussing and declustering fields are always applied within the limits of the free jet 50. As is well known in fluid dynamics, the free jet 50 has a length $y$ along its axis which is given by the relation:

$$y = .69 D \sqrt{\frac{P_o}{P}}$$

where D is the orifice pressure, $P_o$ is the source gas pressure, and P is the background pressure in the vacuum chamber. The end of the free jet is marked by a shock wave beyond which the pressure actually increases. For $P_o = 760$ torr (one atmosphere) and $P = 10^{-3}$ torr, $y = 610D$ (which is much greater than the preferred distance $$X_l = 50D^{+40D}_{-25D}$$

of entrance 108 of lens element 72' from the orifice). The extent of the free jet is determined by available vacuum pumping, and if the pumping is inadequate, the free jet may be terminated by the shock wave before the most desirable region for placing the entrance 108. The vacuum pumping will therefore always be kept sufficient that the shock wave marking the end of the free jet is maintained downstream of the entrance 108 of lens element 72' (typically by distance at least $2X_l$ from the orifice). If the vacuum pumping is sufficient, the free jet 50 can in fact extend to the boundaries of the vacuum stage in which it is located, in which case there is no shock wave. In addition, the cones of the lens elements should present a minimum disturbance to the flow, e.g. they will normally have sharp leading edges and disturb a minimum annular solid angle of the flow, so that they will not themselves produce shock waves.

After the ions enter the free molecular flow region 64' of the free jet, additional focussing lenses may be employed if desired. In the free molecular flow region 64', the gas is so rarified that collisions between ions and molecules are infrequent and the ions cannot acquire a significant additional energy spread. FIG. 9 shows for example a three element Einzel lens 118, having elements 120, 122, 124, which focus the ions into the mass analyzer 52'. In a preferred embodiment of the invention the first element 120 of the Einzel lens was placed at a distance approximately equal to 500D from the orifice. This was within the free jet 50', and specifically was in the free molecular zone 64' of the jet 50'. The first element 120 of the Einzel lens was cone-shaped, to deflect gas away from the ion path, and the conical deflector constituted by element 120 was continued by a further conical deflector 130 (insulated from deflector 120) which continued from the rear edge of element 120 to a position adjacent the cooling fins 46'. The deflectors 120, 130 form a divider between a higher pressure region 132 of the vacuum chamber (about $10^{-3}$ torr) and a lower pressure second region 134, much like divider 82 of FIG. 7. In addition, the cone shaped element 120 in the free jet 50' prevent formation of a shock wave at the end of the free jet in the path of the ion beam 136, hence reducing disturbance of the ion beam and consequent loss of signal. In other words, the arrangement was such as to guide the ion beam 136 out of the free jet 50' without disturbing the prefocussed beam by the shock wave which normally appears at the end of the free jet.

In one mode of operation of the invention the orifice plate 10' was held at between +5 and +60 volts, lens element 72' was grounded, and the first element 120 of the Einzel lens 118 was grounded. Thus there was no electric field applied between the first element 120 of the Einzel lens and lens element 72. Because of the grounded lens element 72' and the grounded cryoshell 126 of the vacuum chamber, the region between the first Einzel lens element 120 and the entrance 108 of the lens element 72' was essentially field free. Actually, some field lines from the middle element 122 of the Einzel lens (which element was held at about 20 volts), may fringe out through the first element 120, but the field produced in this manner is weak (about $\frac{1}{2}$ volt per cm.) and localized near the Einzel lens opening so that it does not extend into a region where numerous collisions between ions and neutral molecules are likely to occur.

The invention also enables ion fragmentation to be caused, under improved conditions which helps to reduce ion fragment energy spread and improve overall ion transmission and hence sensitivity.

If the field between lens element 72' and plate 10' of FIG. 8 is increased, the internal energy acquired by ions due to collisions can become sufficient (e.g. 2.0 to 6.0 ev) to break the chemical bonds in the ions, thus producing ion fragmentation, where the relative abundances of these fragments can be quite similar to the familiar electron impact fragmentation patterns used for species identification in conventional electron impact ion sources on mass spectrometers. While this collisionally induced fragmentation has been observed, caused by collisions with a background gas, this invention allows the fragmentation to be induced in the free jet itself. While the resultant ion energy spread is larger than that resulting from the weaker fields used for declustering, (and hence the ion mass spectrum resolution is degraded to some extent), this fragmentation can nevertheless be very useful for species identification where simple ion mixtures are being analyzed. Typically a voltage in the range between 50 and 200 volts may be applied between the lens 72' and the orifice plate 10' for fragmentation.

In summary, it will be seen that the present invention provides electric fields for focussing and preferably also for declustering, and that these fields are applied in selected regions of the free jet 50, so that the energy spreads acquired by the ions will be held to an acceptable level (depending on the application). No fields (or very weak fields) are applied in the region where the ions can acquire an energy spread which is unacceptable for the application of interest. Beyond this region, i.e. in the free molecular flow zone, further focussing fields may be applied as desired.

What we claim is:

1. A method of focussing ions travelling from a gaseous region through a vacuum chamber to an analyzer in the vacuum chamber, said gaseous region being adjacent said vacuum chamber, said method comprising:

(a) admitting gas from said gaseous region into said vacuum chamber through an orifice in said chamber, said orifice communicating with said gaseous region, (2) maintaining a vacuum in said chamber and maintaining said gas in said gaseous region at a higher pressure so that said gas passes through said orifice and expands from said orifice into said chamber generally in the form of a cone in said chamber and oriented about an axis extending through said orifice with its apex adjacent the orifice, said cone of expanding gas being termed a free jet, the number density in molecules per cubic centimeter of said gas in said free jet being high close to said orifice and falling rapidly with increasing distance from said orifice, the number density of said gas being relatively very low in a vacuum region in said chamber remote from said orifice and said analyzer being in said vacuum region, (3) moving said ions through said orifice into said free jet in said chamber, the expanding gas in said free jet tending to cause said ions to diverge conically, (4) focussing said ions to direct at least some of said ions along a path of travel extending from said orifice into said vacuum region toward said analyzer by applying an electric field to said ions in a selected region which is adjacent said orifice and in said free jet, said field being arranged to direct the paths of at least some of said ions along said path of travel, said selected region being close to said orifice so that the number density of said gas in said selected region is relatively high to limit the kinetic energy spread which ions in said selected region can acquire from accelerations imparted by said electric field, (5) and maintaining the region along said path of travel between said selected region and said vacuum region substantially free of all but weak electric fields, to limit the kinetic energy spread imparted to ions in their travel from said selected region to said analyzer.

2. The method according to claim 1 and including the step of preventing formation of a shock wave in said free jet along said path of travel and thereby limiting disturbance of focussed ions in their travel from said selected region to said analyzer.

3. The method according to claim 2 wherein said free jet has an end which is defined by a shock wave, and including the step of divertng said shock wave away from said path of travel to avoid disturbance by said shock wave of ions moving along said path of travel.

4. The method according to claim 2 wherein said selected region is sufficiently close to said orifice that ions therein cannot acquire a kinetic energy spread greater than about 2 ev therein under said electric field.

5. The method according to claim 2 wherein said electric field applied to said ions in said selected region is of strength such as to accelerate said ions sufficiently that collisions in said selected region between said ions and molecules of said gas tend to cause declustering of said ions.

6. The method according to claim 5 wherein said selected region is such that ions therein can acquire an internal energy of between 0.1 and 1.5 ev but cannot acquire a kinetic energy spread therein greater than about 2 ev, under said electric field therein.

7. The method according to claim 5 wherein the outer limit of said selected region is located at distance $X_f$ from said orifice along said axis, where $$X_l = (50D \pm \frac{40D}{25D}) \sqrt{m},$$

where D is the diameter of said orifice and $m$ is the ratio between the number density of said gas in said gaseous region and $2.7 \times 10^{19}$ molecules per cubic centimeter.

8. The method according to claim 7 and including the step of applying a further focussing electric field to said ions in said vacuum region, said vacuum region being one in which the mean free paths of molecules are at least 2 cm.

9. The method according to claim 8 wherein said region between said vacuum and selected regions is essentially free of electric fields.

10. The method according to claim 2 and wherein said gas is a gas having a vapour pressure substantially less than atmospheric at a predetermined temperature, and including the step of cooling a portion of said vacuum chamber to below said predetermined temperature to condense said gas in said vacuum chamber, thereby cyropumping said gas.

11. The method according to claim 2 and including the step of generating an electric discharge from the tip of a needle located outside said vacuum chamber in said gaseous region and employing said discharge in the production of said ions, and directing said ions through said orifice and through another restricted opening, said opening and orifice being located on said axis and the tip of said needle being located slightly off said axis and thereby reducing radiation entering said vacuum chamber.

12. The method according to claim 11 and including the step of flowing said gas past said needle with the tip of said needle located within such flow, and causing the streamlines of said gas flowing past said tip of said needle to converge as they pass said tip, thereby helping to stabilize said discharge.

13. Apparatus for analyzing trace ions, comprising:
(a) a vacuum chamber having an orifice plate having an orifice therein,
(b) means for providing said trace ions in a source gas adjacent said orifice plate,
(c) means for maintaining a vacuum in said chamber so that said gas will expand into said chamber in the form of a free jet which is oriented about an axis through said orifice and which is of length at least equal to $2X_l$, where $X_l$ is hereinafter defined,
(d) means for moving said ions, with some of said gas, along said axis through said orifice into said vacuum chamber,
(e) a mass analyzer in said vacuum chamber and spaced from said orifice,
(f) an electrostatic lens element in said vacuum chamber, said lens element being of truncated conical shape having a sharp leading edge,
(g) means mounting said lens element with its projected apex aimed approximately at said orifice and with the distance $X_l$ between the entrance to said lens element and said orifice being:

$$X_l = [50D \pm \frac{40D}{25D}] \sqrt{m}$$

where D is the diameter of said orifice and $m$ is the ratio between the number density of said gas and $2.7 \times 10^{19}$ molecules per cubic centimeter.

14. Apparatus according to claim 13 wherein said means (a) includes an electric discharge needle having a second axis, said analyzer includes an ion detector having an entrance aperture spaced substantially from said orifice and located on said first mentioned axis, and means mounting said needle with said second axis offset slightly from said first mentioned axis.

15. Apparatus according to claim 14 and further including a shroud enclosing said needle and having an outlet opening, said tip of said needle being centred in said outlet opening, means for directing gas through said shroud and past the tip of said needle and out said outlet opening, the inner surface of said shroud converging inwardly at said outlet opening to cause the streamlines of gas flowing through said shroud to converge inwardly as they pass said tip of said needle, to help stabilize a discharge from the tip of said needle.

16. An electric discharge source for creating ions from a gas comprising:
(a) a needle having a tip,
(b) a cylindrical shroud having an outlet opening, said needle being within said shroud and said tip being located at said outlet opening, said needle and shroud defining an annular space therebetween,
(c) means for directing a stream of said gas through said annular space over said needle and then past said needle tip,
(d) means for applying a potential difference between said needle tip and an electrode spaced from said needle tip to create an electric discharge at said needle tip, to ionize molecules in said gas passing said tip,
(e) the inner surface of said shroud converging inwardly adjacent said outlet opening to cause the steamlines of said gas to converge as they pass said needle tip, whereby to help stabilize said discharge.

17. A method of producing ions from a gas comprising: generating an electric discharge from the tip of a needle, said needle extending along an axis and terminating at said tip, flowing said gas over said needle in the direction of said axis and then past said tip of said needle, whereby said discharge will ionize molecules in said gas passing said tip, and causing the streamlines of said gas flowing past said tip of said needle to converge as they pass said tip, thereby helping to stabilize said discharge.

* * * * *